United States Patent
Ohmae et al.

(10) Patent No.: US 6,687,532 B2
(45) Date of Patent: Feb. 3, 2004

(54) OPTICAL CT APPARATUS AND IMAGE RECONSTRUCTING METHOD

(75) Inventors: Etsuko Ohmae, Hamamatsu (JP); Yukio Ueda, Hamamatsu (JP); Yutaka Yamashita, Hamamatsu (JP)

(73) Assignee: Hamamatsu Photonics K.K., Shizouka (JP)

( * ) Notice: Subject to any disclaimer, the term of this patent is extended or adjusted under 35 U.S.C. 154(b) by 0 days.

(21) Appl. No.: 09/997,179

(22) Filed: Nov. 30, 2001

(65) Prior Publication Data

US 2002/0099287 A1 Jul. 25, 2002

Related U.S. Application Data

(63) Continuation-in-part of application No. PCT/JP99/02960, filed on Jun. 3, 1999.

(51) Int. Cl.$^7$ ............................................. A61B 5/05
(52) U.S. Cl. ..................... 600/425; 600/407; 600/310; 356/432; 356/337; 250/341.1
(58) Field of Search ................................ 600/310, 407, 600/425; 382/131; 356/432, 337; 250/341.1

(56) References Cited

U.S. PATENT DOCUMENTS

| | | | |
|---|---|---|---|
| 5,402,778 A | 4/1995 | Chance | 128/633 |
| 5,441,054 A | 8/1995 | Tsuchiya | 128/665 |
| 5,596,987 A | 1/1997 | Chance | 128/633 |
| 5,813,988 A | * 9/1998 | Alfano et al. | 600/476 |
| 5,835,617 A | * 11/1998 | Ohta et al. | 382/131 |
| 5,905,261 A | * 5/1999 | Schotland et al. | 250/341.8 |
| 5,907,406 A | 5/1999 | Papaioannou et al. | 356/432 |
| 6,104,946 A | * 8/2000 | Tsuchiya et al. | 600/476 |

FOREIGN PATENT DOCUMENTS

| | | |
|---|---|---|
| JP | 3-146850 | 6/1991 |
| JP | 4-241850 | 8/1992 |
| JP | 5-18856 | 1/1993 |
| JP | 6-129984 | 5/1994 |
| JP | 7-5101 | 1/1995 |
| JP | 7-303633 | 11/1995 |
| JP | 8-29329 | 2/1996 |
| JP | 8-304229 | 11/1996 |
| JP | 10-185815 | 7/1998 |

OTHER PUBLICATIONS

H.L. Graber et al., "Imaging of Multiple Targets in Dense Scattering Media," SPIE vol. 2570, pp. 219–234.

Brian W. Pogue et al., "Forward and Inverse Calculations for 3–D Frequency–Domain Diffuse Optical Tomography," SPIE vol. 2389, pp. 328–339.

S.R. Arridge et al., "Performance of an Iterative Reconstruction Algorithm for Near Infrared Absorption and Scatter Imaging," SPIE vol. 1888, pp. 360–371.

* cited by examiner

*Primary Examiner*—George Manuel
*Assistant Examiner*—Barry Pass
(74) *Attorney, Agent, or Firm*—Morgan, Lewis & Bockius LLP

(57) ABSTRACT

An optical CT apparatus 10 is mainly composed of a container 12 filled with an optical interface member 20; a light-projecting section, comprising a light source 22 and an optical switch 24, for projecting light into the container 12; a light-detecting section, comprising photodetectors 30 and shutters 32, for detecting the light from the inside of the container 12; and an arithmetic/control section 14 for calculating a spatial distribution of absorption coefficient. The arithmetic/control section 14 has a function of determining a spatial distribution of a characteristic amount concerning a part of an object to be measured 200 according to a comparison of an optical intensity signal actually measured by each detector 30 in a state where the container 12 is filled with the optical interface member 20 with an optical signal actually measured by each detector 30 in a state where the optical interface member 20 is partly replaced by the part of object to be measured 200.

15 Claims, 14 Drawing Sheets

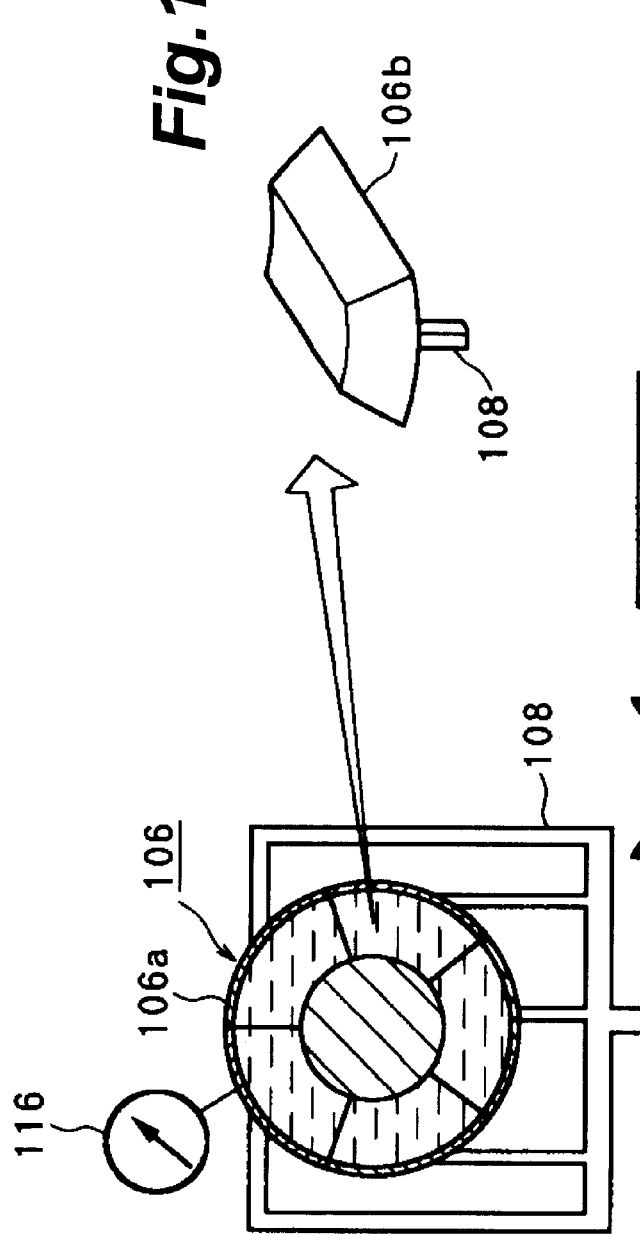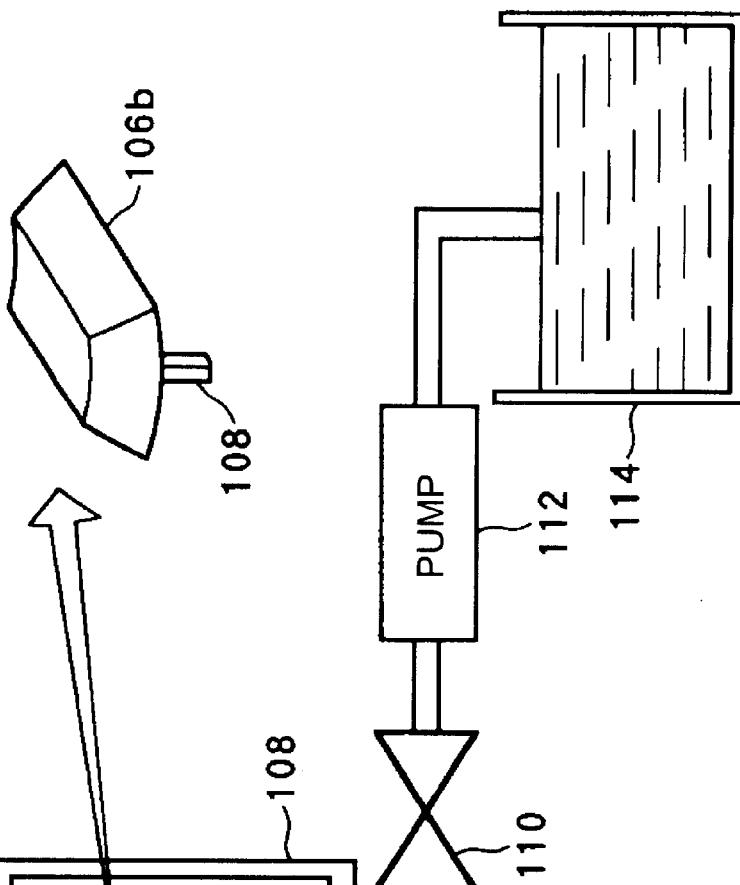

OPTICAL CT APPARATUS AND IMAGE RECONSTRUCTING METHOD

RELATED APPLICATION

The present application is a continuation-in-part application of PCT application No. PCT/JP99/02960 filed on Jun. 3, 1999, designating U.S.A. and now pending.

BACKGROUND OF THE INVENTION

1. Field of the Invention

The present invention relates to an optical CT apparatus and image reconstructing method for projecting light to a part of an object to be measured such as an organism or the like, and calculating a spatial distribution of a characteristic amount concerning an optical characteristic of the part of object to be measured from a characteristic amount concerning an optical characteristic of the light transmitted therethrough.

2. Related Background Art

X-ray CT, ultrasonic CT, MRI, and the like have currently been in use as clinical image diagnosing apparatus. In addition, attention has recently been given to optical CT because of the fact that near infrared light exhibits a high transmissivity with respect to biological tissues, that it can measure the oxygen concentration in biological tissues, that it is safer than X-rays and the like, and so forth.

An optical CT apparatus is mainly composed of a light-projecting section for projecting light to each location of a part of an object to be measured; a light-detecting section for measuring the intensity of light projected from the light-projecting section and transmitted through the part of object to be measured; and an arithmetic section for reconstructing an absorption coefficient distribution image within the part of object to be measured from thus measured optical intensity and optical path.

Known as an example of image reconstructing methods is the following one by R. L. Barbour et al ("Imaging of Multiple Targets in Dense Scattering Media" (H. L. Graber, J. Chang, R. L. Barbour, SPIE Vol. 2570, p. 219-p. 234)). Namely, this is a method in which light beams are projected from a plurality of locations on a surface of a part of an object to be measured toward the inside of the part of object to be measured and, from the optical path length calculated in each of volume elements into which the part of object to be measured is divided, the absorption material concentration of each volume element is determined. Here, it is necessary to use another phantom having an outer shape identical to that of the part of object to be measured but with no absorption therein, so as to measure a standard value of the detection intensity (transmission light intensity).

The above-mentioned image reconstructing method makes it possible to determine the absorption material concentration of each volume element, whereby the absorption coefficient distribution image within the part of object to be measured can be reconstructed by displaying thus determined concentration as a grayscale image, for example.

On the other hand, Japanese Patent Application Laid-Open No. HEI 6-129984 discloses that a medium (hereinafter referred to as optical interface member) having a refractive index and a scattering coefficient which are substantially the same as those of the part of object to be measured is interposed between the light-projecting section and the part of object to be measured, so as to prevent light from being reflected, scattered, and so forth on the surface of the part of object to be measured, thereby raising the accuracy in measurement.

SUMMARY OF THE INVENTION

However, the above-mentioned image reconstructing method and the optical CT apparatus using the above-mentioned image reconstructing method have problems as follows.

First, in the above-mentioned image reconstructing method, it is necessary to prepare another phantom having an outer shape identical to that of the part of object to be measured but with no absorption therein in order to measure a standard value of the detection intensity. As a consequence, a different phantom must be prepared when measuring a different part of object to be measured, which remarkably increases the measurement time. When the part of object to be measured has a complicated structure such as an organism, preparing such a phantom is difficult in terms of measurement accuracy, and thus is unrealistic.

Second, since the above-mentioned image reconstructing method uses the optical path length calculated in each of a plurality of volume elements into which the part of object to be measured is divided, so as to reconstruct an absorption coefficient distribution image within the part of object to be measured, it is necessary, when measuring a part of an object to be measured having a different outer shape, to redivide the part of object to be measured into a plurality of minute volume elements and recalculate the optical path length in each volume element. Therefore, it takes a considerable time to reconstruct the image.

It is an object of the present invention to overcome the above-mentioned problems and provide an optical CT apparatus and image reconstructing method which can rapidly reconstruct the absorption coefficient distribution image within the part of object to be measured.

For overcoming the above-mentioned problems, the optical CT apparatus of the present invention comprises a container accommodating a light-transparent medium therein; light-projecting means for projecting light into the container from at least one part of the container; light-detecting means for detecting the light projected by the light-projecting means in at least one part of the container; and arithmetic means for calculating a spatial distribution of a characteristic amount of a part of an object to be measured according to a comparison of a characteristic amount concerning an optical characteristic of the light transmitted through the medium actually measured by use of the light-projecting means and the light-detecting means in a state where the medium is accommodated within the container with a characteristic amount concerning an optical characteristic of the light transmitted through the medium and/or the part of object to be measured actually measured by use of the light-projecting means and the light-detecting means in a state where the medium is partly replaced by the part of object to be measured.

Also, for overcoming the above-mentioned problems, the image reconstructing method of the present invention comprises a first measurement step of projecting light from at least one part of a container accommodating a light-transparent medium therein into the container by using light-projecting means, and detecting the light projected by the light-projecting means in at least one part of the container by using light-detecting means, so as to obtain a characteristic amount concerning an optical characteristic of the light transmitted through the medium; a second measurement step of projecting light from at least one part of the container into the container by using the light-projecting means in a state where the medium accommodated within the container is partly replaced by a part of an object to be measured, and detecting the light projected by the light-projecting means in at least one part of the container by using the light-detecting means, so as to obtain a characteristic amount concerning an optical characteristic of the light transmitted through the medium and/or the part of object to be measured; and an arithmetic step of calculating, according to a comparison of the characteristic amount concerning the optical characteristic of the transmitted light obtained by the first measurement step with the characteristic amount concerning the optical characteristic obtained by the second measurement step, a spatial distribution of a characteristic amount concerning an optical characteristic of the part of object to be measured.

When a container having a predetermined form is used, and a spatial distribution of a characteristic amount concerning an optical characteristic of a part of an object to be measured is calculated according to a comparison of a characteristic amount concerning an optical characteristic of transmitted light measured in a state filled with a medium with a characteristic amount concerning an optical characteristic of transmitted light measured in a state where the medium is partly replaced by the part of object to be measured as in the configuration mentioned above, it becomes unnecessary to prepare another phantom having a shape identical to that of the part of object to be measured but with no absorption therein so as to prepare a standard amount. Also, it becomes unnecessary to redivide a part of an object to be measured having a different outer shape into minute volume elements and recalculate the optical path length in each volume element. As a result, the measurement time can greatly be shortened, so that the absorption coefficient distribution image within the part of object to be measured can rapidly be reconstructed.

BRIEF DESCRIPTION OF THE DRAWINGS

FIGS. 15A and 15B are views showing an eighth modified example of the container.

DESCRIPTION OF THE PREFERRED EMBODIMENTS

Figure 1:
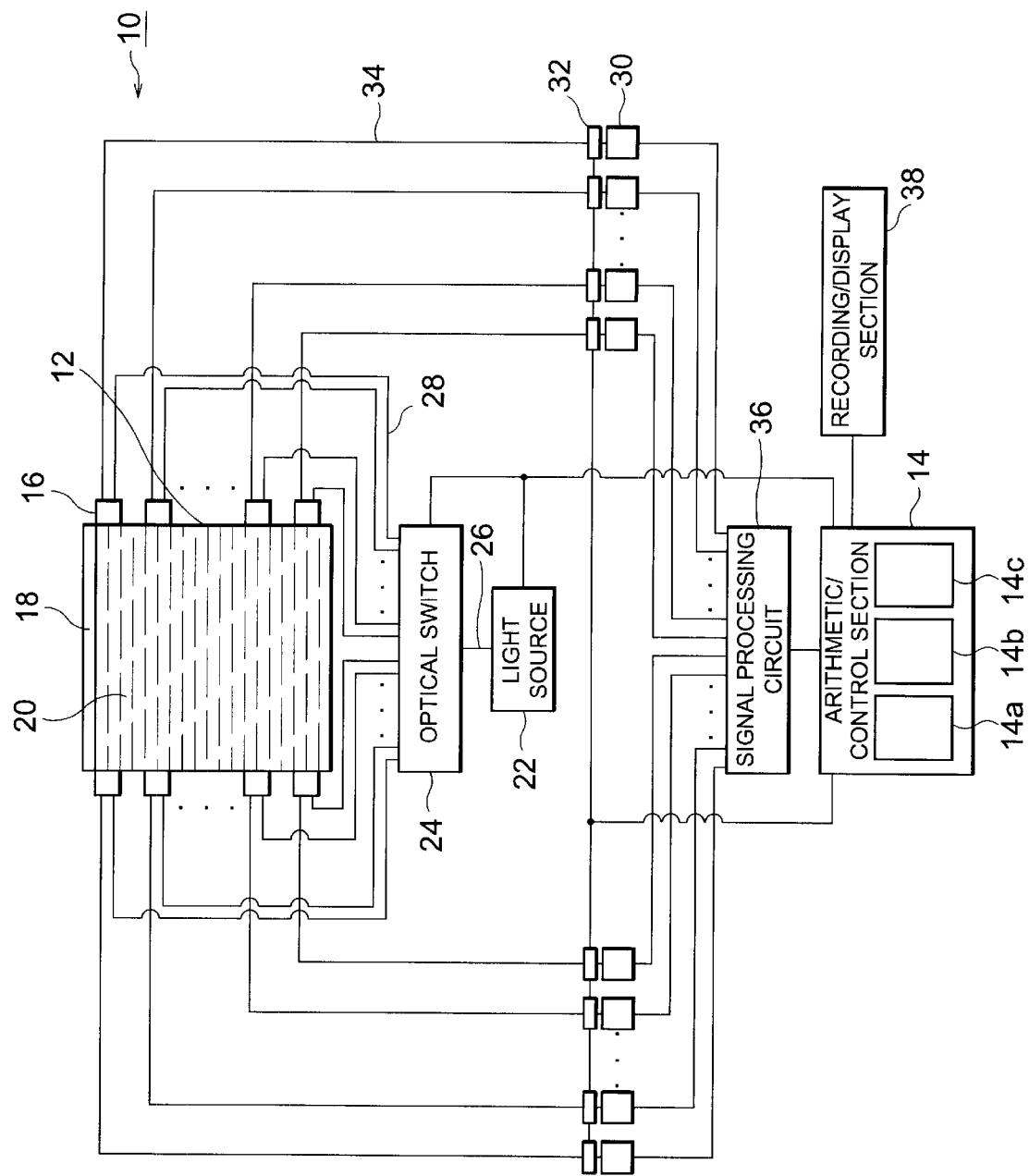
FIG. 1 is a system diagram of the optical CT apparatus in accordance with an embodiment of the present invention.
Figure 2:
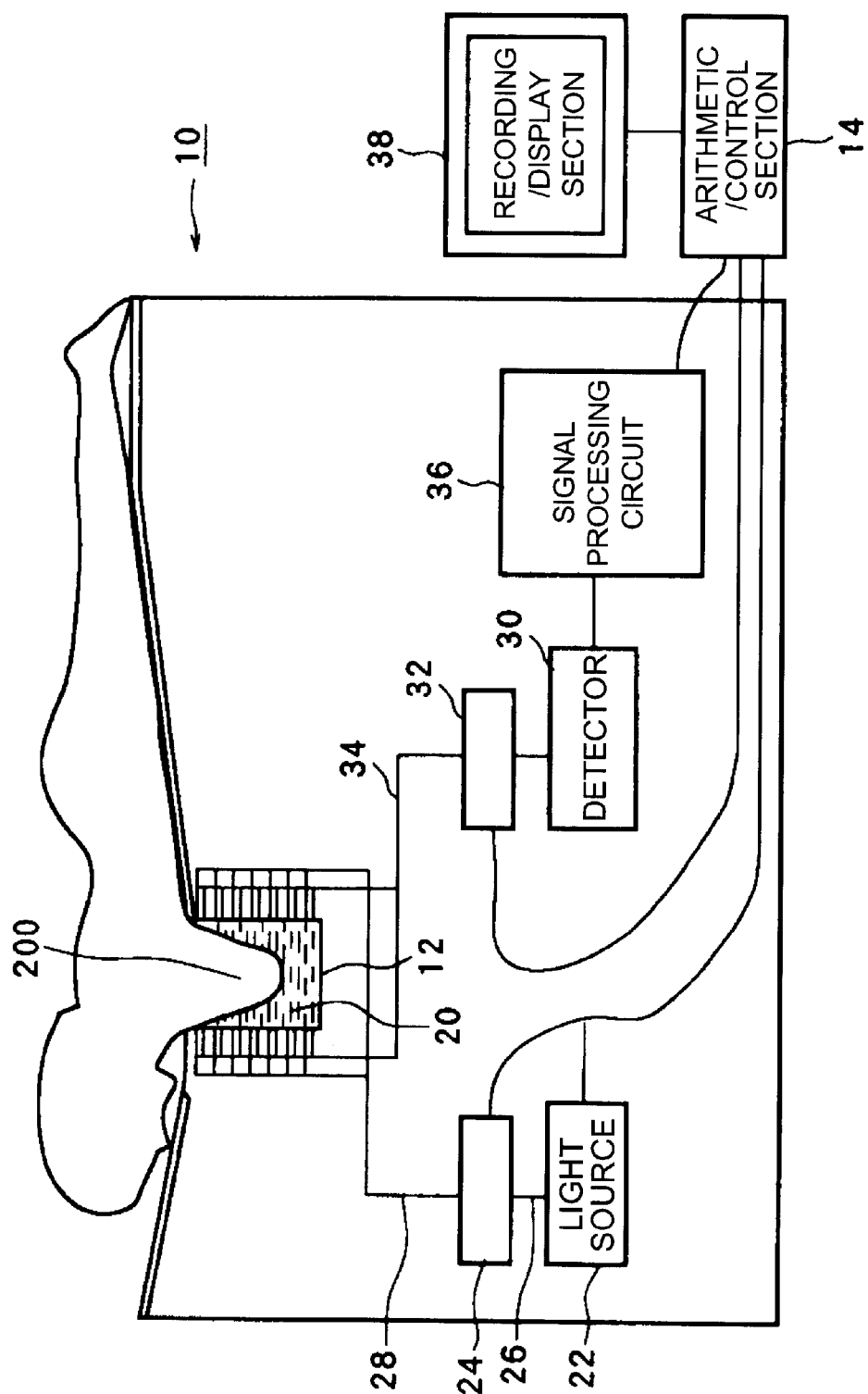
FIG. 2 is a view showing a state in which the optical CT apparatus in accordance with the embodiment of the present invention is used.
Figure 3:
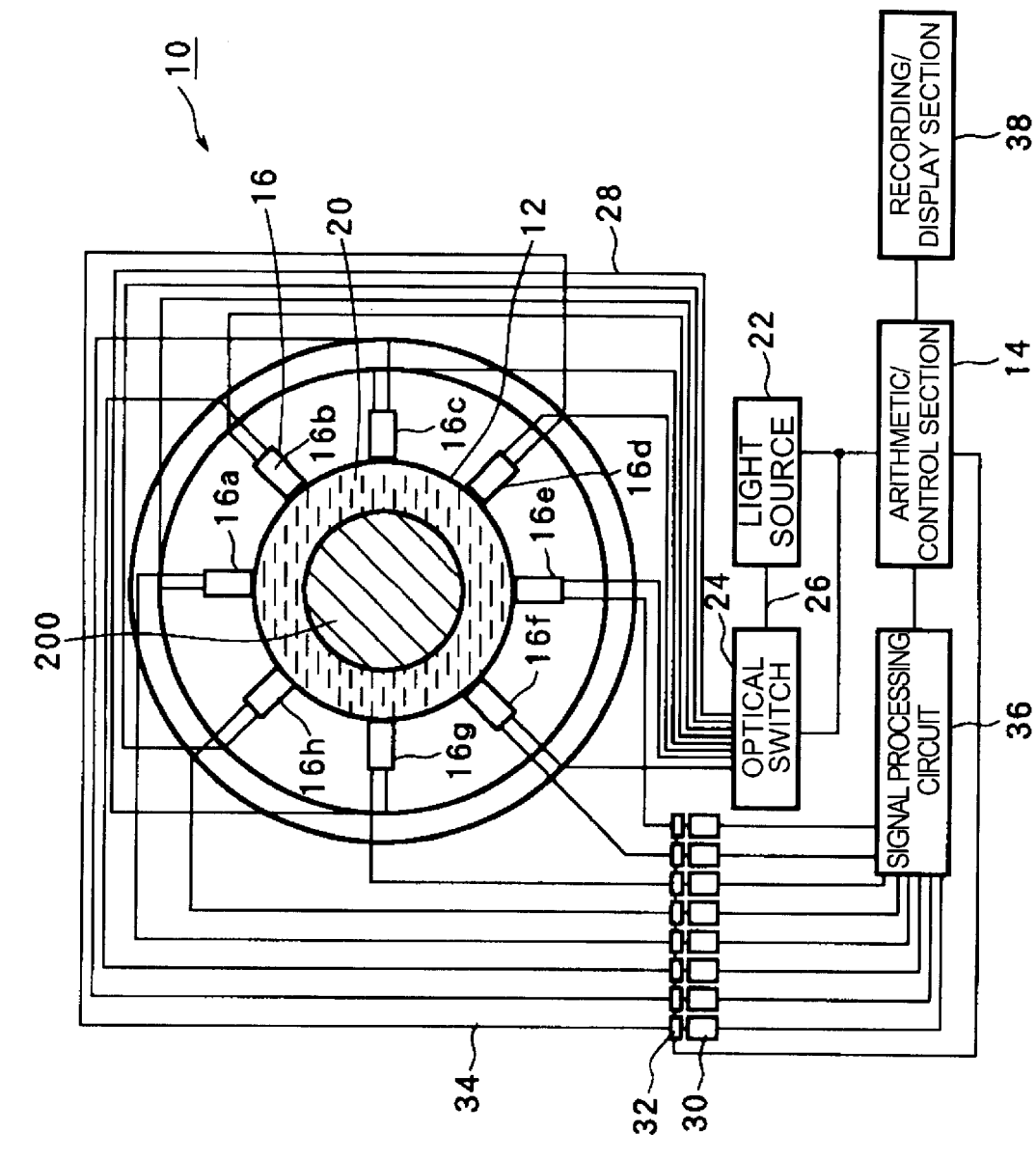
FIG. 3 is a diagram of the optical CT apparatus in accordance with the embodiment of the present invention about its container.

The optical CT apparatus in accordance with an embodiment of the present invention will be explained with reference to the drawings. First, the configuration of the optical CT apparatus in accordance with the embodiment of the present invention will be explained. FIG. 1 is a system diagram of the optical CT apparatus in accordance with the embodiment of the present invention, FIG. 2 is a view showing a state where the optical CT apparatus in accordance with the embodiment of the present invention is used, and FIG. 3 is a diagram of the optical CT apparatus in accordance with the embodiment of the present invention about its container. The optical CT apparatus 10 is mainly composed of a container 12 for accommodating a part of an object to be measured 200, a light-projecting section for projecting light into the container 12, a light-detecting section for detecting the light projected by the light-projecting section, and an arithmetic/control section 14 for calculating a spatial distribution of an absorption coefficient of the part of object to be measured 200 from the quantity of light detected by the light-detecting section.

The container 12 has such a size that the part of object to be measured 200 (the part of object to be measured 200 being assumed to be a female breast in this embodiment as shown in FIG. 2) can fully be accommodated, and has a cylindrical form having an opening portion in the upper face thereof. In the side face of the container 12, n (n being an integer of 2 or more) light-projecting/detecting ports 16 are three-dimensionally arranged at positions different from each other in depth and circumferential directions of the container 12 (see FIG. 3), so that light can be projected into various depths and various directions within the container 12, and light can be detected from various depths and various directions within the container 12. Also, the container 12 is formed from a light-shielding material, so as to prevent light from entering the container 12 from portions other than the light-projecting/detecting ports 16. Further, the opening portion of the container 12 can be covered with a light-shielding plate 18, which prevents the light from entering the container 12 from the opening portion.

The container 12 is filled with an optical interface member 20. The optical interface member 20 is a material which fills the gap between the part of object to be measured 200 and the container 12, thereby acting to reduce the discontinuity of an optical characteristic in the surface of the part of object to be measured 200. Specifically, it refers to a medium having at least one characteristic selected to from optical characteristics such as absorption coefficient, scattering coefficient, refractive index, optical rotation, and polarization degree is made substantially identical to the average value of absorption coefficient, average value of scattering coefficient, average value of refractive index, average value of optical rotation, average value of polarization degree, or the like in the part of object to be measured 200. Employed in the case where the part of object to be measured 200 is a human body is, for example, a medium whose optical characteristics are caused to match those of the part of object to be measured 200 by dissolving silica, Intralipid (fat emulsion), or the like for attaining the desirable scattering coefficient, ink or the like having a particular absorption coefficient at a specific wavelength for attaining the desirable absorption coefficient, glucose, fructose, or the like for attaining the desirable optical rotation and polarization degree into water having a refractive index substantially identical to that of the human body. Here, "substantially identical" refers to the cases where they are identical or can be regarded as identical from the viewpoint of measurement accuracy or the like.

The light-projecting section is constituted by a light source 22 and an optical switch 24. The light source 22 uses a semiconductor laser, thereby being able to supply projection light. The optical switch 24 is a one-input/n-output optical switch and is capable of selectively connecting one of projection optical fibers 28, which are connected to then light-projecting/detecting ports 16, to the light source 22 in order to guide the light inputted by way of a light-source optical fiber 26 to the n light-projecting/detecting ports 16 individually and exclusively.

The light-detecting section is constituted by n photodetectors 30 and shutters 32 disposed in front of respective input sections of the photodetectors. Detected light beams are fed into the n photodetectors 30 from the n light-projecting/detecting ports 16 by way of detection optical fibers 34, whereby respective optical densities in the light-projecting/detecting ports 16 can be detected individually and exclusively.

Provided behind the detectors 30 is a signal processing circuit 36 for A/D-converting the optical intensities detected by the detectors 30, and feeding thus obtained signals into the arithmetic/control section 14.

The arithmetic/control section 14 has a function of determining a spatial distribution of the absorption coefficient of the part of object to be measured 200 according to a comparison of the optical intensity signal actually measured by each detector 30 in the state where the container 12 is filled with the optical interface member 20 with the optical intensity signal actually measured by each detector 30 in the state where the optical interface member 20 is partly replaced by the part of object to be measured 200. Namely, the arithmetic/control section 14 comprises a first arithmetic section 14a for assuming the inside of the container 12 to be an assembly model divided into a plurality of volume elements and calculating a degree of influence of a change in a characteristic amount concerning an optical characteristic of each volume element upon a characteristic amount concerning an optical characteristic of transmitted light detected by the light-detecting section in the case where the light-projecting section and light-detecting section are used; a second arithmetic section 14b for calculating an amount obtained when an optical amount concerning an optical characteristic of the light transmitted through the optical interface member 20 actually measured by use of the light-projecting section and light-detecting section in the state where the optical interface member 20 is accommodated within the container 12 and an optical amount concerning an optical characteristic of the light transmitted through the optical interface member 20 and/or the part of object to be measured 200 actually measured by use of the light-projecting section and light-detecting section in the state where the optical interface member 20 is partly replaced by the part of object to be measured 200 are compared with each other; and a third arithmetic section 14c for calculating a spatial distribution of a characteristic amount concerning an optical characteristic of the part of object to be measured 200 by calculating a characteristic amount concerning an optical characteristic of each volume element from the degree of influence determined by the first arithmetic section 14a and the amount obtained by the second arithmetic section 14b from the comparison of the characteristic amounts concerning optical characteristics. More specific algorithms will be mentioned in detail in the image reconstructing method, which will be explained later. The arithmetic/control section 14 also has a function of controlling the emission of the light source, actions of the optical switches 24, and opening/closing of the shutters 32.

The optical CT apparatus 10 further comprises a recording/display section 38, thus being capable of storing the detected optical intensity signal temporarily and visualizing the spatial distribution of the absorption coefficient of the part of object to be measured 200 calculated by the arithmetic/control section 14 by grayscale display, color-coding display, and the like.

Figure 4:
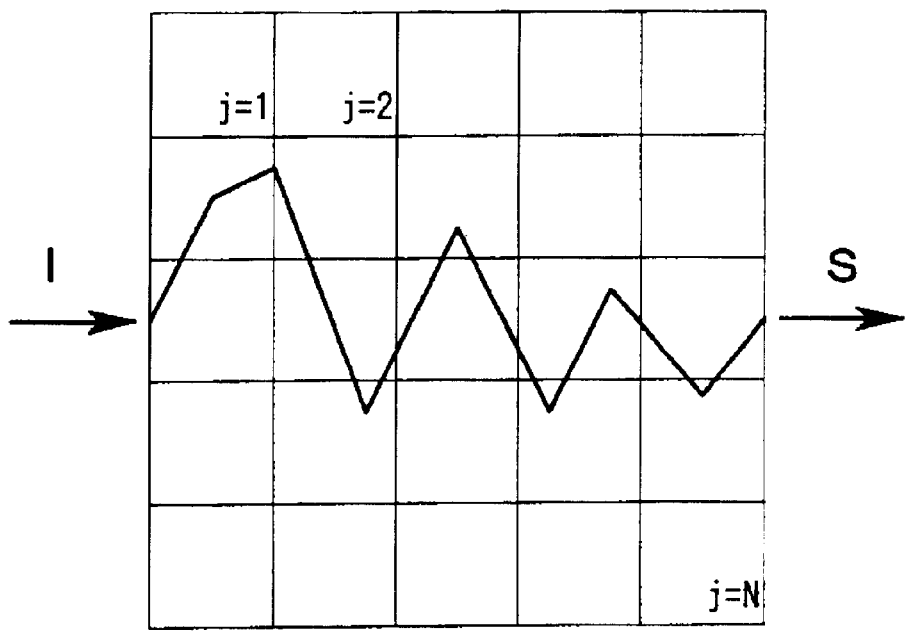
FIG. 4 is a chart showing how light is transmitted through a medium having a uniform absorption coefficient.
Figure 5:
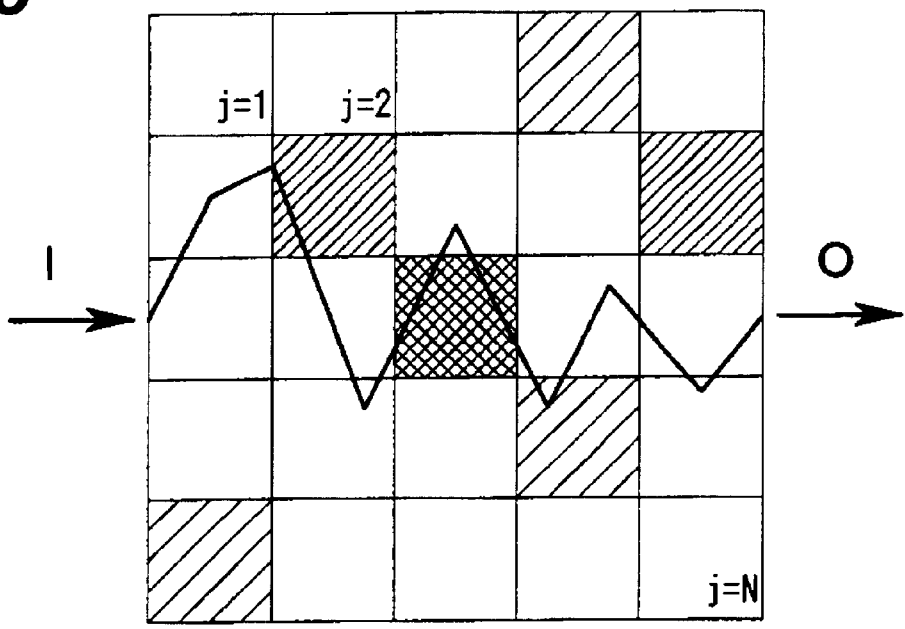
FIG. 5 is a chart showing how light is transmitted through a medium having a nonuniform absorption coefficient.

The basic principle of the image reconstructing method in accordance with this embodiment will now be explained. FIG. 4 is a chart showing how light is transmitted through a medium having a uniform absorption coefficient, whereas FIG. 5 is a chart showing how light is transmitted through a medium having a nonuniform absorption coefficient. For simplification, a medium which is a scattering absorber is assumed to be a two-dimensionally expanding square and is divided into N (=25) square volume elements (which are area elements to be exact since they are two-dimensional) having the same size. It is assumed that the absorption coefficient is constant within each volume element whereas the absorption coefficient of the volume elements marked with hatches and the like is different from that of the other volume elements.

In the case where light is projected from a point of a medium having a uniform absorption coefficient (the absorption coefficient being $\mu_a$) into the medium whereas the output light is detected at one point as shown in FIG. 4, the detection intensity S is expressed by:

$$S = D_{sr} \cdot I \cdot \exp\{-\mu_a(W_1 + W_2 \ldots + W_N)\} \quad (1)$$

where I is the incident intensity, $W_j$ (j=1 to N) is the degree of influence of each volume element, and $D_{sr}$ is the attenuation constant indicating the ratio by which the incident light is let out of the medium upon scattering, reflection, and the like. Here, the degree of influence of each volume element refers to the ratio by which the detection intensity is changed when the absorption coefficient of each volume element changes in the case where light is projected from a certain point and then is detected at a certain point, whereas a specific method of calculating the same will be explained later.

The absorption coefficient of each volume element of a medium having different absorption coefficients $\mu_{aj}$ (j=1 to N) in the respective volume elements as shown in FIG. 5 is expressed by:

$$\mu_{aj} = \mu_a + \Delta\mu_{aj} \quad (j=1,2,\ldots,N) \quad (2)$$

where $\mu_a$ is a reference absorption coefficient, and $\Delta\mu_{aj}$ (j =1 to N) is the change of the absorption coefficient of each volume element from $\mu_a$. Assuming that the attenuation constant $D_{sr}$ is unchanged from that in the case where the absorption coefficient is constant, the detection intensity O in this case is expressed as:

$$O = D_{sr} \cdot I \cdot \exp\{-[W_1(\mu_a + \Delta\mu_{a1}) + W_2(\mu_a + \Delta\mu_{a2}) + \ldots + W_N(\mu_a + \Delta\mu_{aN})]\} \quad (3)$$

$$= S \cdot \exp\{-(W_1\Delta\mu_{a1} + W_2\Delta\mu_{a2} + \ldots + W_N\Delta\mu_{aN})\}$$

Therefore, by taking logarithms of both sides of expression (3), the following expression is obtained:

$$\ln S - \ln O = (W_1 \Delta\mu_{a1} + W_2 \Delta\mu_{a2} + \ldots + W_N \Delta\mu_{aN}) \quad (4)$$

$$= \sum_{j=1}^{N} W_j \Delta\mu_{aj}$$

Here, expression (4) becomes a function of the detection intensity S (hereinafter referred to as reference intensity S) of light projected from one point of the medium having a uniform absorption coefficient and outputted to one point, the detection intensity O (hereinafter referred to as measurement intensity O) of light projected from one point of the medium having a nonuniform absorption coefficient and outputted to one point, the degree of influence $W_j$ (j=1 to N) within each volume element, and the change $\Delta\mu_{aj}$ (j=1 to N) of the absorption coefficient of each volume element from $\mu_a$. Among these variables, the reference intensity S and the measurement intensity O are obtained by measurement, whereas the degree of influence $W_j$ (j=1 to N) is obtained by a calculation (details of which will be explained later), whereby only N pieces of the change $\Delta\mu_{aj}$ (j=1 to N) of the respective absorption coefficients of volume elements from $\mu_a$ are left as unknown quantities. Therefore, when N pieces of equations each represented by expression (4) are simultaneously formed concerning different sets of light-projecting points/light-detecting points, N pieces of $\Delta\mu_{aj}$ can be determined, which makes it possible to calculate the spatial distribution of the absorption coefficient of the medium.

Specifically, assuming $S_i$ to be the reference intensity in the i-th (i=1 to N) set of light-projecting point/light-detecting point, $O_i$ to be the detection intensity, and $W_{ij}$ (j=1 to N) to be the degree of influence of each volume element, expression (4) is represented as indicated by expression (5):

$$\ln S_i - \ln O_i = \sum_{j=1}^{N} W_{ij} \Delta\mu_{aj} \quad (5)$$

Here, expressions (5) for all instances of i are arranged and represented in the form of matrix as:

$$\begin{pmatrix} \ln S_1 - \ln O_1 \\ \ln S_2 - \ln O_2 \\ \vdots \\ \vdots \\ \ln S_N - \ln O_N \end{pmatrix} = \begin{pmatrix} W_{11} & W_{12} & \cdots & \cdots & W_{1N} \\ W_{21} & W_{22} & & & \vdots \\ \vdots & & \ddots & & \vdots \\ \vdots & & & \ddots & \vdots \\ W_{N1} & \cdots & \cdots & \cdots & W_{NN} \end{pmatrix} \begin{pmatrix} \Delta\mu_{a1} \\ \Delta\mu_{a2} \\ \vdots \\ \vdots \\ \Delta\mu_{aN} \end{pmatrix} \quad (6)$$

Therefore, n pieces of $\Delta\mu_{aj}$, i.e., the spatial distribution of absorption coefficient of the medium, can be determined as indicated by expression (7):

$$\begin{pmatrix} \Delta\mu_{a1} \\ \Delta\mu_{a2} \\ \vdots \\ \vdots \\ \Delta\mu_{aN} \end{pmatrix} = \begin{pmatrix} W_{11} & W_{12} & \cdots & \cdots & W_{1N} \\ W_{21} & W_{22} & & & \vdots \\ \vdots & & \ddots & & \vdots \\ \vdots & & & \ddots & \vdots \\ W_{N1} & \cdots & \cdots & \cdots & W_{NN} \end{pmatrix}^{-1} \begin{pmatrix} \ln S_1 - \ln O_1 \\ \ln S_2 - \ln O_2 \\ \vdots \\ \vdots \\ \ln S_N - \ln O_N \end{pmatrix} \quad (7)$$

Here, how to determine the degree of influence $W_{ij}$ (j =1 to N) of each volume element will be explained. The steady-state light diffusing equation of continuous light (luminous flux) incident on each volume element is:

$$\Delta\Phi - \mu_a D^{-1}\Phi = 0 \quad (8)$$

where $\Phi$ is the luminous flux (optical density per unit volume);

$\mu_a$ is the optical absorption coefficient of each volume element;

$\mu_s'$ is the optical isotropic scattering coefficient of each volume element; and D is the diffusion coefficient of each volume element $$\left(D = \frac{1}{3\mu_s'}\right).$$

The boundary condition between the inside and outside of the medium is:

$$\Phi_{BL} = 0 \quad (9)$$

Here, the suffix BL indicates the boundary between the inside and outside of the medium. Also, expression (9) is equivalent to such a condition that light is completely absorbed by this boundary, e.g., a state where the surroundings of the medium are painted pitch-black.

Using expressions (8) and (9), a light transmission simulation (hereinafter referred to as first simulation) is carried out with respect to each set of light-projecting point/light-detecting point, i.e., the i-th (i=1 to N) set of light-projecting point/light-detecting point, whereby the detection light intensity is calculated. In the first simulation, however, the medium is assumed to have a constant absorption coefficient $\mu_s$, complete diffusion is assumed in the above-mentioned expression (8), and the size of the container 12 is greater than $1/\mu_s'$. The detection intensity in the i-th (i=1 to N) set of light-projecting point/light-detecting point obtained by the first simulation is assumed to be $d_{i0}$.

Subsequently, using expressions (8) and (9), a second simulation is carried out. In the second simulation, assuming that one volume element of the medium has an absorption coefficient $\mu_a + \Delta\mu_a$ which is different from the absorption coefficient $\mu_a$, a light transmission simulation is carried out with respect to each set of light-projecting point/light-detecting point. For example, it is assumed that $\Delta\mu_a = 0.01$ mm$^{-1}$. Under this condition, the detection light intensity is calculated. The detection intensity in the case where the absorption coefficient of the j-th (j =1 to N) volume element is changed with respect to the i-th (i=1 to N) set of light-projecting point/light-detecting point is assumed to be $d_{ij}$.

Using the detection light quantities calculated by the first and second simulations, the degree of influence $W_{ij}$ of each volume element is represented as indicated by expression (10):

$$W_{ij} = \mu_a^{-1} \ln(d_{i0}/d_{ij}) \quad (10)$$

Consequently, $W_{ij}$ is determined from expression (10), whereby the spatial distribution of absorption coefficient is calculated from expression (7).

Referring to FIG. 3, the image reconstructing method in accordance with an embodiment of the present invention will now be explained. The image reconstructing method in accordance with this embodiment includes a first measurement step of measuring a reference intensity in a state where the container 12 is filled with the optical interface member 20; a second measurement step of measuring a measurement intensity O in a state where the optical interface 20 is partly replaced by the part of object to be measured 200 (e.g., a human breast); and an arithmetic step of calculating a spatial distribution of absorption coefficient of the part of object to be measured 200 according to a comparison between the reference intensity S and measurement intensity O.

In the first measurement step, the reference intensity S is measured. First, the inner space of the container 12 is divided into volume elements. The number of divided volume elements can arbitrarily be determined in view of the spatial resolution necessary for the absorption coefficient to be determined, the processing performances of the arithmetic/control section 14 and recording/display section 38, and the like. Namely, the number of divided volume elements may be made greater when the absorption coefficient distribution is to be measured at a higher resolution, whereas the number of divided volume elements may be made smaller when the measurement speed and processing speed are in preference to the resolution. Though the inner space of the container 12 can be divided into volume elements after the reference intensity and measurement intensity O are measured, unknown quantities occur by the number of divided volume elements in this case, which makes it desirable to set forth equations by a number identical to the number of divided volume elements, whereby it is preferred that the number of divided volume elements be determined beforehand.

After the inner space of the container 12 is divided into volume elements, actual measurement is carried out. The container 12 is filled with the optical interface member 20 having a known absorption coefficient $\mu_a$, whereas the opening portion of the container 12 is blocked with the light-shielding plate 18 in order to prevent light from entering from parts other than the light-projecting/detecting ports 16. In this state, the light emitted from the light source 22 is projected into the container 12 individually and exclusively from the light-projecting/detecting ports 16a to 16h upon switching the optical switch 24. The emission of the projection light in the light source 22 and the switching of the optical switch 24 are controlled by the arithmetic/control section 14.

The light projected into the container 12 is guided to the photo detectors 30 from the light-projecting/detecting ports 16, whereby the respective light quantities incident on the light-projecting/detecting ports 16a to 16h are detected individually and exclusively. Here, when the intensity of detection light incident on the light-projecting/detecting ports 16 at positions for projecting light is remarkably high, it is preferable to close the shutters 32 at the corresponding positions in order to protect the photodetectors 30.

When 8 pieces of light-projecting/detecting ports 16a to 16h are provided as shown in FIG. 3, 8×8=64 ways of combinations are possible as sets of light-projecting points/light-detecting points. However, measured values cannot be obtained when the incident detection light intensity becomes remarkably high in combinations in which a projecting port and a detecting port are located at the same position (e.g., a combination in which light is projected from the light-projecting/detecting port 16a and is detected by the same light-projecting/detecting port 16a), since the shutter 32 is closed because of the reason mentioned above. In a pair of combinations in which projecting ports and detecting ports are positioned opposite from each other (e.g., a combination in which light is projected from the light-projecting/detecting port 16a and is detected at the light-projecting/detecting port 16e, and a combination in which light is projected from the light-projecting/detecting port 16e and is detected at the light-projecting/detecting port 16a), one of them is excluded since they yield the same data. In general, one of them may be excluded when such an optical reciprocity theorem holds, whereas they are treated as different data when the optical reciprocity theorem does not hold.

When measurement is carried out by arbitrarily selecting sets of light-projecting/light-detecting points by the number identical to the number of divided volume elements among the sets of light-projecting points/light-detecting points, the quantity of detection light in the i-th set is A/D-converted by the signal processing circuit 36, so as to be fed as the reference intensity $S_i$ into the arithmetic/control section 14 and stored into the recording/display section 38.

In the second measurement step, the measurement intensity O is measured. The measuring method is basically the same as the above-mentioned measurement of the reference intensity S, whereby the detection intensity is measured with respect to the sets of light-projecting points/light-detecting points selected at the time of measuring the reference intensity S. At the time of measuring the measurement intensity O, however, the measurement is carried out while the optical interface member 20 accommodated within the container 12 is partly replaced by the part of object to be measured 200. When the measurement is carried out, the detection intensity in the i-th set is A/D-converted by the signal processing circuit 36, so as to be fed as the measurement intensity $O_i$ into the arithmetic/control section 14 and stored in the recording/display section 38.

The human breast, which is the part of object to be measured 200, is accommodated within the container 12 as shown in FIG. 2. Though the whole opening portion of the container 12 cannot be covered with the shielding plate 18 in this case, the gap between the part of object to be measured 200 and the fringe part of the opening portion of the container 12 can be covered with the shielding plate 18 when necessary.

The arithmetic step includes a first arithmetic step of calculating the degree of influence of each volume element; a second arithmetic step of calculating an amount obtained when the reference intensity $S_i$ and the measurement intensity $O_i$ are compared with each other; and a third arithmetic step of calculating the absorption coefficient of each volume element from the degree of influence of each volume element determined by the first arithmetic step and the amount obtained from the comparison of optical intensities determined by the second arithmetic step.

The first arithmetic step is a step of calculating the degree of influence $W_{ij}$ of the j-th volume element in the i-th set of light-projecting point/light-detecting point. The specific method of calculating $W_{ij}$ is as already explained. This calculation determines an N×N matrix of degree of influence [W] as indicated by expression (11):

$$[W] = \begin{pmatrix} W_{11} & W_{12} & \cdots & \cdots & W_{1N} \\ W_{21} & W_{22} & & & \vdots \\ \vdots & & \ddots & & \vdots \\ \vdots & & & \ddots & \vdots \\ W_{N1} & \cdots & \cdots & \cdots & W_{NN} \end{pmatrix} \quad (11)$$

In the second arithmetic step, an amount obtained from the comparison between the reference intensity $S_i$ and measurement intensity $O_i$ in the i-th set of light-projecting point/light-detecting point is calculated. Specifically, as this amount of comparison, the difference between the natural logarithm of the reference intensity $S_i$ and the natural logarithm of the measurement intensity $O_i$ is calculated for each set of light-projecting point/light-detecting point, whereby an N×1 measurement matrix [SO] shown in expression (12) is determined:

$$[SO] = \begin{pmatrix} \ln S_1 - \ln O_1 \\ \ln S_2 - \ln O_2 \\ \vdots \\ \vdots \\ \ln S_N - \ln O_N \end{pmatrix} \quad (12)$$

In the third arithmetic step, using expression (7), the absorption coefficient of each volume element is calculated from the matrix of degree of influence [W] calculated in the first arithmetic step and the measurement matrix [SO] calculated in the second arithmetic step. Here, the amount determined from expression (7) is the amount of change from the reference absorption coefficient $\mu_a$ to be exact, whereas the absorption coefficient $\mu_a$ of the optical interface member 20 is known, whereby the absolute value of absorption coefficient can easily be obtained.

Thus obtained absorption coefficient of each volume element is outputted as an absorption coefficient distribution image from the recording/display section 38.

Effects of the optical CT apparatus and image reconstructing method in accordance with the embodiment of the present invention will further be explained. The optical CT apparatus and image reconstructing method in accordance with the present invention uses a container 12 having a fixed form, measures a reference intensity in a state where the container 12 is filled with an optical interface member 20, and measures the measurement intensity in a state where the optical interface member 20 is partly replaced by the part of object to be measured 200. Therefore, it becomes unnecessary to prepare another phantom having a shape identical to that of the part of object to be measured 200 but with no absorption therein so as to measure the reference intensity, whereby the measurement time is greatly shortened in the case where different parts of objects to be measured 200 are measured, while the measurement accuracy improves. Once the degree of influence of each volume element is calculated while the inner space of the container 12 having a fixed form is divided into volume elements, it becomes unnecessary to recalculate the matrix of degree of influence even when the form of the part of object to be measured 200 or the like is changed as in the case where another part of object to be measured 200 is used, whereby image reconstruction at a very high speed is possible.

Also, since the optical interface member 20 is inserted into the gap between the light-projecting/detecting ports 16 and the part of object to be measured 200, the optical CT apparatus and image reconstructing method of the present invention can prevent light from leaking, internal blood metabolisms from changing due to the blood stasis and the like occurring from the pressure to the part of object to be measured 200, and reflections and the like from occurring on the surface of the part of object to be measured 200, whereby measurement with a high accuracy is possible.

Further, since the measurement time can be shortened so that pressure pains and marks can be prevented from remaining due to pressures to the part of object to be measured 200 as mentioned above, the psychological and physical burdens on the subject can be alleviated.

Also, since the optical interface member 20 is used, even when light having a strong directivity and a high energy is emitted from the light source 22, the light scatters within the optical interface member 20, whereby the part of object to be measured can be irradiated with a safe and large amount of light.

Though the case where the number of equations indicated by expression (4) is identical to the number of volume elements is explained in the above-mentioned embodiment, specific problems can be converted into unspecific problems by use of a singular value decomposition method and the like whether the number of equations is greater or smaller than the number of volume elements, whereby the spatial distribution of absorption coefficient of the part of object to be measured 200 can be determined.

Though a semiconductor laser is used for the light source 22 in the above-mentioned embodiment, solid-state lasers, dye lasers, and gas lasers may also be used therefor. Further, light selected in terms of wavelength by a wavelength selector from light from LED or a white light source may be used therefor.

Though an analyzing method in the case where continuous light is used as projection light is explained in the above-mentioned embodiment, methods described in "performance of an iterative reconstruction algorithm for near infrared absorption and scatter imaging" (S. R. Arridge, M. Schweiger, M. Hiraoka, D. T. Delpy, SPIE Vol. 1888, p. 360-p. 371) and "Forward and Inverse Calculations for 3-D Frequency-Domain Diffuse Optical Tomography" (Brain W. Pogue, Michael S. Patterson and Tom J. Farrell, SPIE Vol. 2389, p. 328-p. 339), for example, may also be used with respect to cases utilizing an analyzing method for determining the moment of a time-resolved waveform obtained by time-resolved spectroscopy (TRS) employing pulsed light and an analysis method of phase difference method (PMS) employing phase-modulated light.

Figure 6:
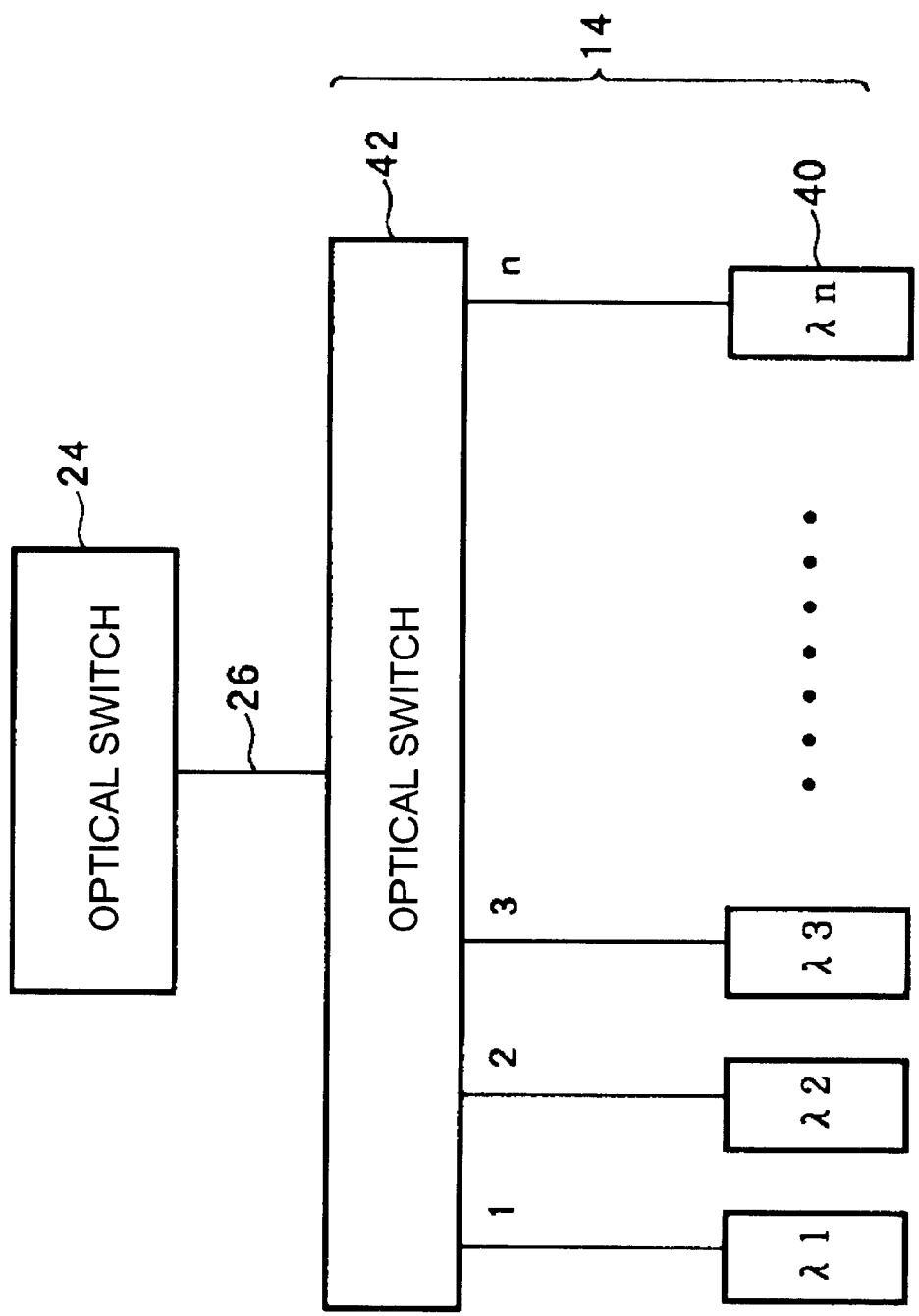
FIG. 6 is a diagram of a wavelength-selecting switch.

Not only a single wavelength of light but also two or more kinds of wavelengths of light can selectively be used as projection light. In the latter case, a wavelength-variable laser may be used, the wavelength in use may be changed by use of a wavelength selector, or a light source 14 having light sources 40 for respectively projecting wavelengths λ1 to λn of light and an optical switch 42 for choosing a wavelength by selectively switching the individual light sources 40 as shown in FIG. 6 may be used.

Though the optical CT apparatus 10 of the above-mentioned embodiment comprises a plurality of light-projecting ports and a plurality of light-detecting ports by the same number (n), a single light-projecting port and a plurality of light-detecting ports may be provided if a required measurement accuracy is satisfied. Similarly, a single light-detecting port and a plurality of light-projecting ports may be provided.

Though the part of object to be measured 200 is assumed to be a human breast in this embodiment, it can similarly be used in cases where the head, hands, feet, body, and the like are measured.

As for the optical interface member 20, one made of a liquid-like or gel-like material adapted to solidify as the time passes may be used as well. When the optical interface member 20 made of a material adapted to solidify as the time passes is used, the measuring section can be fixed, whereby the measurement accuracy improves, and the burden on the subject can be reduced since measurement can be carried out in a relaxed posture.

Though the optical interface member 20 employed in this embodiment is made of a material in which at least one characteristic selected from its optical characteristics, i.e., absorption coefficient, scattering coefficient, refractive index, optical rotation, and polarization degree is made substantially identical to the average value of absorption coefficient, average value of scattering coefficient, average value of refractive index, average value of optical rotation, average value of polarization degree, or the like in the part of object to be measured 200, the spatial distribution of absorption coefficient of the part of object to be measured 200 can also be determined when the absorption coefficient, scattering coefficient, refractive index, optical rotation, polarization degree, and the like are not substantially identical to those of the part of object to be measured 200 by carrying out corrections using known values if the absorption coefficient, scattering coefficient, refractive index, optical rotation, polarization degree, and the like are known.

Also, when a method for measuring a three-dimensional form of the part of object to be measured 200, such as laser scanning, for example, is used therewith, a known absorption coefficient can be used in the part filled with the optical interface member 20, whereby the accuracy in calculation at the time when solving expression (7) improves. Further, the part in which the optical interface member 20 is incorporated can be assumed to be one volume element, whereby the number of volume elements to be divided can be reduced.

Though the absorption coefficient of the part of object to be measured 200 is measured in the above-mentioned embodiment, it is also applicable to the measurement of the scattering coefficient, refractive index, fluorescent characteristic, and the like of the part of object to be measured 200.

Though the above-mentioned embodiment measures the absorption coefficient of the part of object to be measured 200 by using the optical intensity of the transmitted light, it is also applicable to measurement using the phase and time-resolved waveform of transmitted light.

Figure 7:
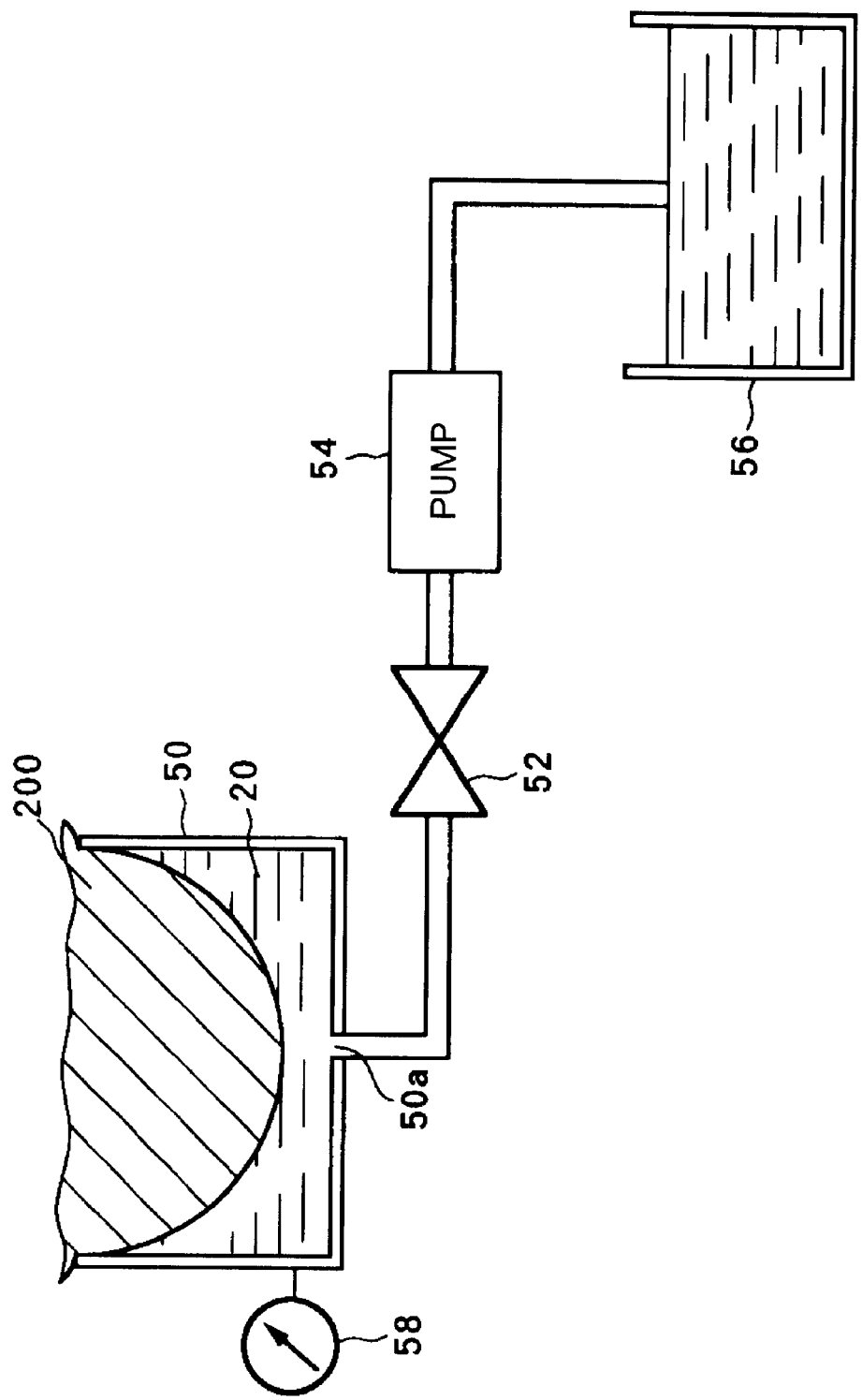
FIG. 7 is a view showing a first modified example of the container.

Modified examples of the container used in the optical CT apparatus in accordance with this embodiment will now be explained. FIG. 7 shows a first modified example of the container. The container 50 is one which can reduce the pressure therewithin. The container 50 contains the optical interface member 20 therein, and has such an opening portion that the part of object to be measured 200 can be introduced therethrough. The bottom part of the container 50 is formed with a suction port 50a for drawing the optical interface member 20 to the outside, whereas a valve 52, a pump 54, and a reservoir 56 are provided by way of a pipe. Also, the container 50 is provided with a pressure gauge 58 for measuring the pressure of the optical interface member 20 within the container 50.

When the container 50 is used, in the state where the optical interface member 20 is accommodated within the container while the part of object to be measured 200 is further introduced therein, the valve 52 is opened, and the optical interface material 20 within the container 50 is drawn toward the reservoir 56 by use of the pump 54. At that time, the pressure within the container 50 can be monitored by the pressure gauge 58. When the measurement of the part of object to be measured 200 is terminated, the optical interface member 20 can also be returned from the reservoir 56 toward the container 50.

When thus configured container 50 is used in the case of a breast cancer inspection in which the part of object to be measured 200 is a breast, measurement can be carried out over a wide range by increasing the measurement volume upon reducing the pressure when the breast is small. When the container 50 has a shape in which an armpit can also be inserted, the rib and flesh can be separated from each other by reducing the pressure within the container 50, whereby the vicinity of a lymph node and the like where a cancer is likely to occur can be measured accurately.

Figure 8:
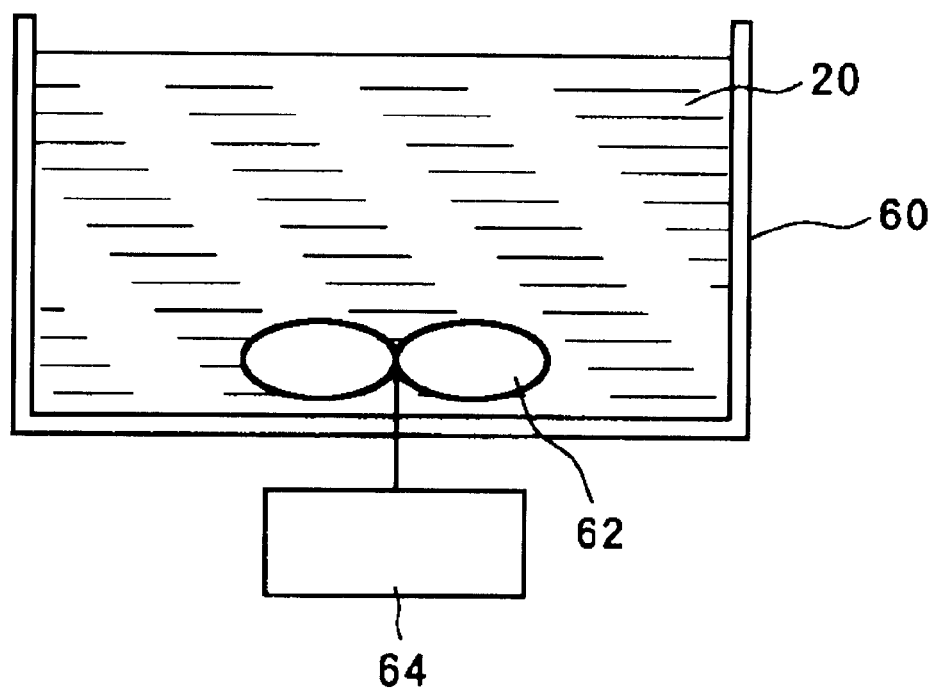
FIG. 8 is a view showing a second modified example of the container.

FIG. 8 shows a second modified example of the container. The container 60 shown in FIG. 8 comprises a propeller 62 for stirring the optical interface member 20 accommodated within the container 60, and a motor 64 for driving this propeller.

Stirring the optical interface member 20 by use of the propeller 62 makes it possible to homogenize the state of the optical interface member 20 within the container 60, thereby reducing errors in measurement. Other methods for stirring the optical interface member 20 include one in which the inner wall of the container 60 is formed with minute holes, through which air flows or water flows are gushed into the container 60.

Figure 9:
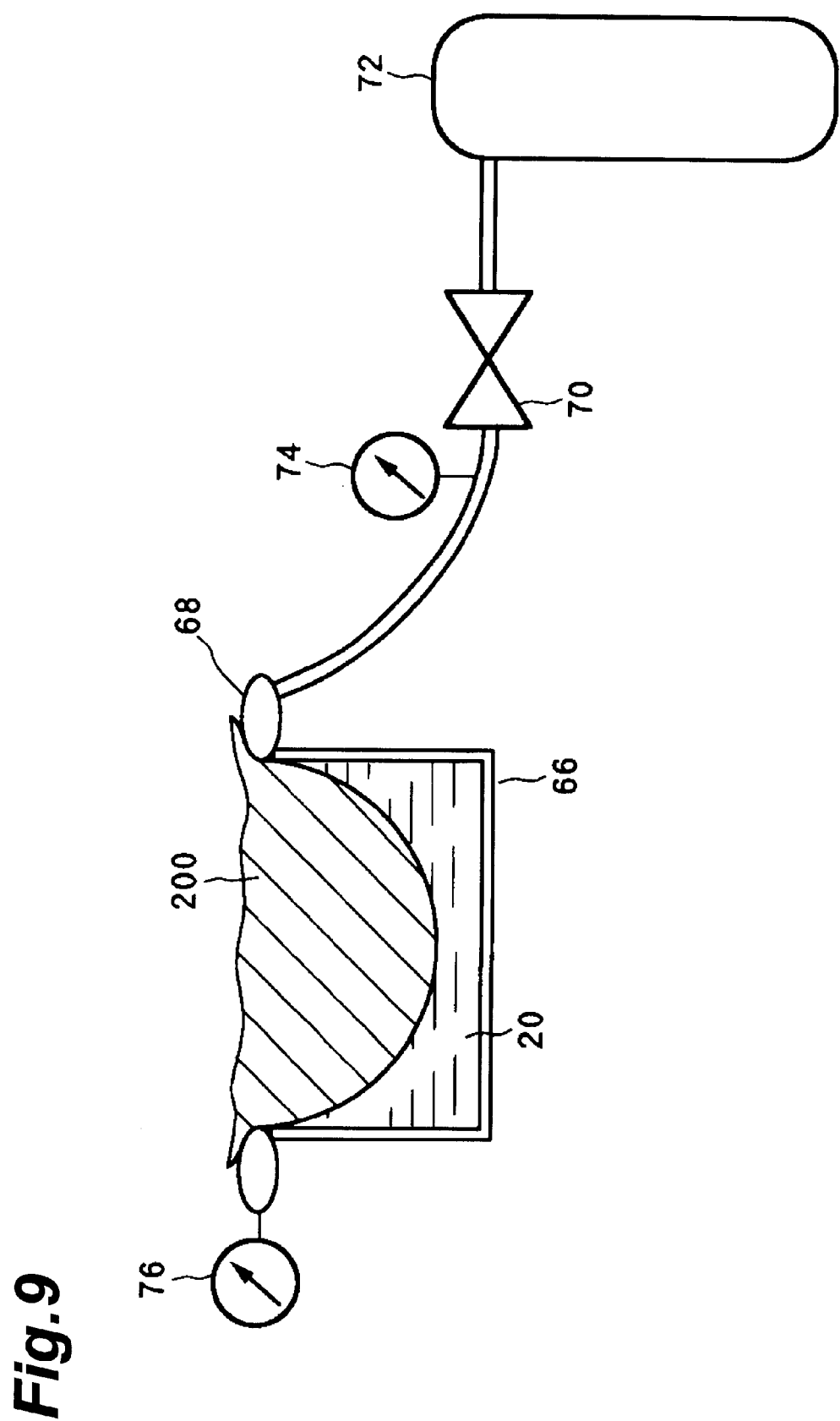
FIG. 9 is a view showing a third modified example of the container.

FIG. 9 shows a third modified example of the container. The container 66 shown in FIG. 9 is one having a deformable light-shielding member in the opening portion of the container in order to block the light from the outside. An airbag 68 made of a light-shielding material is provided at the fringe part of the opening portion of the container 66. The airbag 68 is connected to an air cylinder 72 by way of a valve 70, whereby air can be injected into the airbag 68. The amount of injection of air into the airbag 68 can be measured by a flow meter 74 provided downstream the valve 70, whereas a pressure gauge 76 for measuring the pressure within the airbag 68 is also provided.

In this container 66, the airbag 68 inflates due to the air injected from the air cylinder 72, and thus inflated airbag 68 covers the gap between the opening portion of the container 66 and the part of object to be measured 200, whereby the light entering from the outside and causing errors in measurement can completely be shut out. Also, a portion of the part of object to be measured 200 is kept from directly abutting against the fringe part of the opening portion of the container 66, whereby pressure pains and pressures on the contact part are alleviated.

Figure 10:
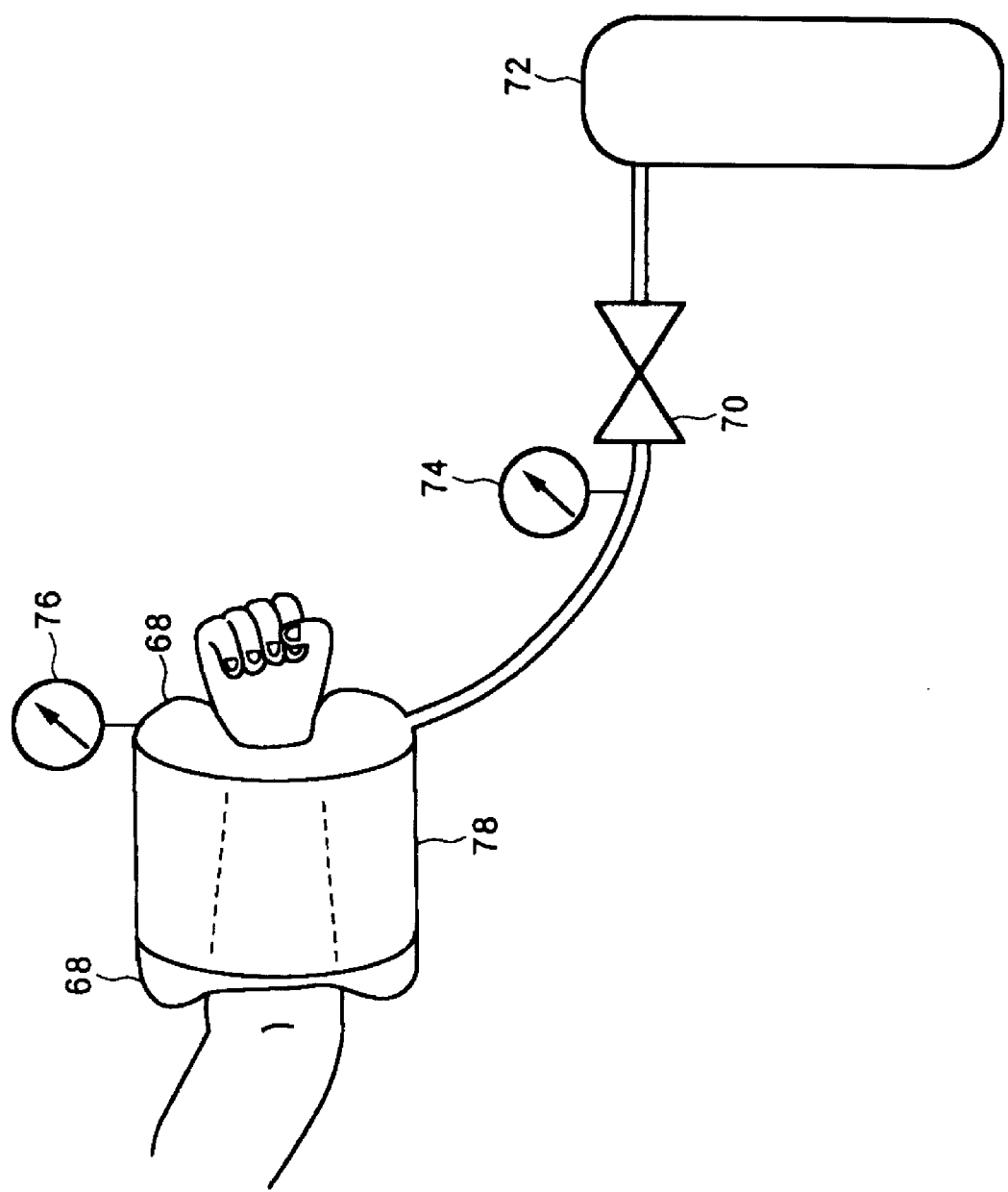
FIG. 10 is a view showing a fourth modified example of the container.

FIG. 10 shows a fourth modified example of the container. Its basic structure is similar to that of the container 66, which is the above-mentioned third embodiment, in that it has a deformable light-shielding member in the opening portion of the container, but differs therefrom in that the container 78 of this modified example has two opening portions whereas the container 66 of the third modified example has a single opening portion.

When a container having two or more opening portions is used, arms, feet, the body, and the like can be inserted through the container, whereby center parts of the arms, feet, and body and the like can be measured.

Figure 11:
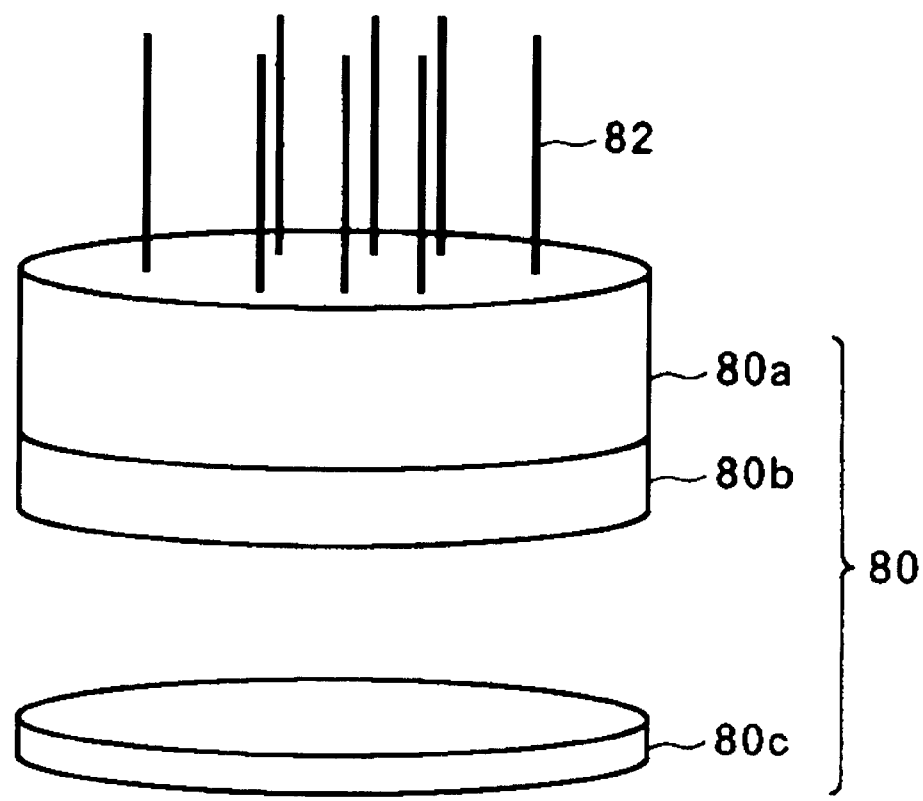
FIG. 11 is a view showing a fifth modified example of the container.

FIG. 11 shows a fifth example of the container. The container of this modified example is used when measuring diffused reflected light on the same plane as the entrance surface, for example, as in the measurement of abdomen. The container 80 is constituted by a first part 80a having a columnar form with only one bottom face opened whereas the other bottom face is provided with light-projecting/detecting optical fibers 82, a second part 80b having a columnar form with both bottom faces opened while having a height identical to the inner depth of the part of object to be measured 200, and a light-shielding plate 80c.

When measuring the reference intensity S by use of the container 80, the measurement is carried out in a state where the opening portion of the first part 80a and one opening portion of the second part 80b are connected to each other, the optical interface member 20 is introduced into the first part 80a and second part 80b, and the other opening portion of the second part 80b is closed with the light-shielding plate 80c.

Figure 12:
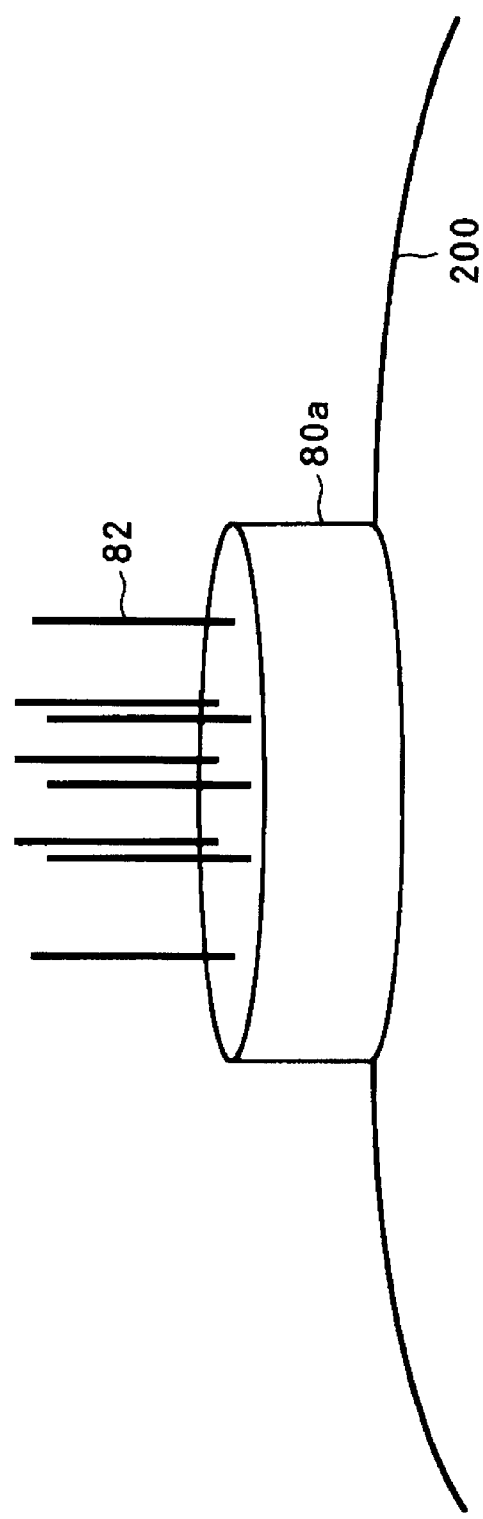
FIG. 12 is a view showing the state of use of the container in the fifth modified example.

When measuring the measurement intensity O, on the other hand, the measurement is carried out in a state where the optical interface member 20 is introduced into the first part 80a while the opening portion thereof is in contact with the surface of the part of object to be measured 200 as shown in FIG. 12.

Using this container also makes it possible to measure the absorption coefficient within the part of object to be measured 200 that cannot be accommodated within a container having a fixed form.

Figure 13:
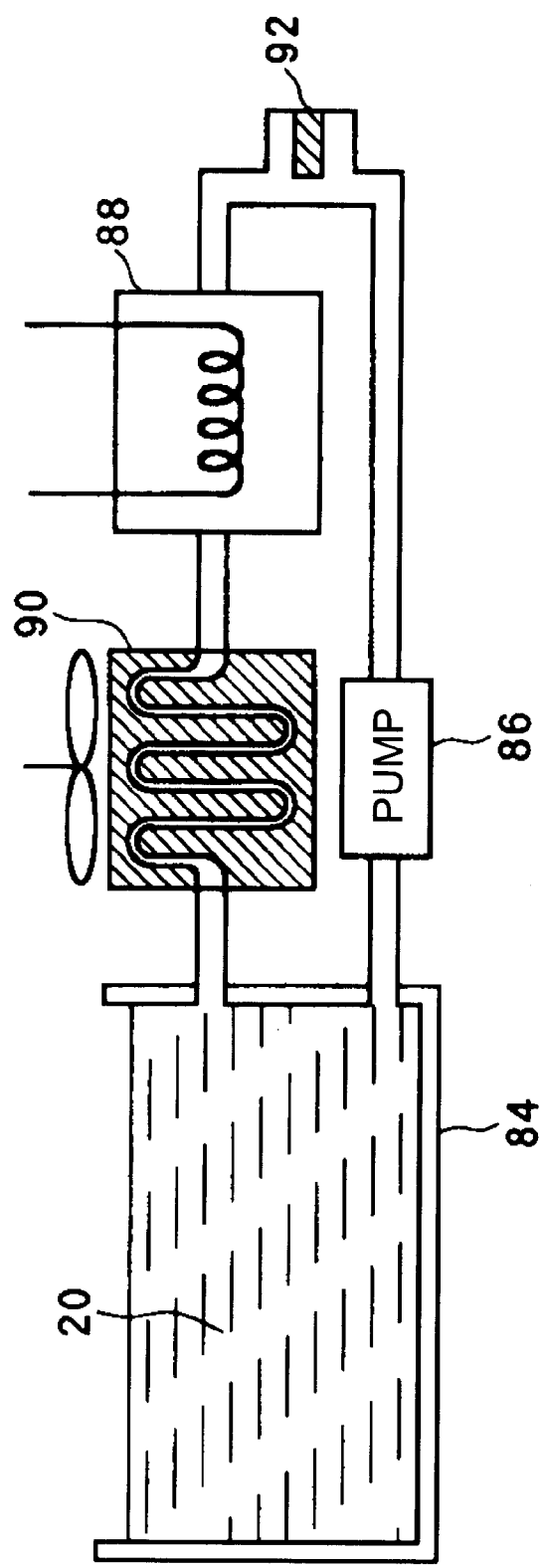
FIG. 13 is a view showing a sixth modified example of the container.

FIG. 13 shows a sixth modified example of the container. The container of this modified example is one which can uniformly keep the temperature of the optical interface member 20. This container 84 is formed from a material having a thermal insulation effect, and is configured such that the optical interface member 20 contained therein can be circulated through a heater 88 and a cooler 90 by way of a pump 86. A temperature sensor 93 is provided in the circuiting path, whereas the heater 88 and the cooler 90 are controlled according to the output of the temperature sensor 92 by an external computer which is not depicted or the like.

Using such a container 84 makes it possible to keep the temperature of the optical interface member 20 and reduce errors in measurement caused by changes in temperature, while preventing the subject from feeling uneasy.

Figure 14:
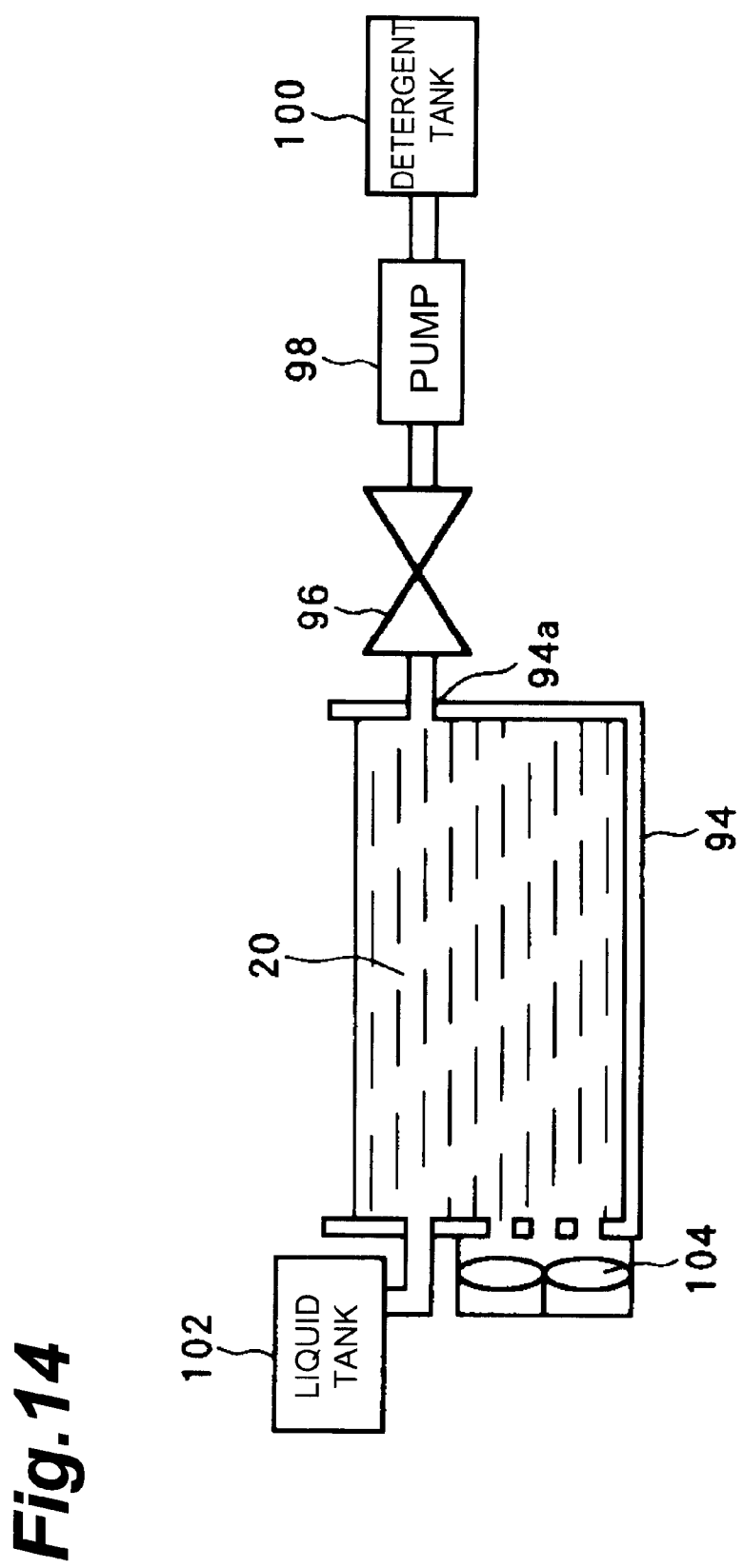
FIG. 14 is a view showing a seventh modified example of the container.

FIG. 14 shows a seventh modified example of the container. The container of this modified example is one which can remove the optical interface member 20 attached to the inside of the container after the measurement. A pump 98 and a detergent tank 100 are connected to this container 94 by way of a valve 96, whereby a detergent can be supplied from a detergent injection port 94a into the container 94. Also, a liquid tank 102 storing washing water there within is provided, so that the washing water can be supplied into the container 94 and wash the inside of the container 94 and the part of object to be measured 200. Further, the side wall of the container 94 is provided with a fan 104, so that the inside of the container 94 and the part of object to be measured 200 can be dried.

FIGS. 15A and 15B show an eighth modified example of the container. The container of this modified example is used in a case where a forearm part is measured, for example. This container 106 is constituted by an undeformable cylindrical container outer wall 106a (see FIG. 15A) made of a light-shielding material, and a plurality of deformable bags 106b (see FIG. 15B) made of a transparent material. A tube 108 is connected to each bag 106b, so that the latter is connected by way of a valve 110 to a pump 112 and a reservoir 114 storing the optical interface member 20. Also, a pressure gauge 116 for measuring the pressure within the bag 106b is provided.

When the container 106 is used, the valve 110 is opened in a state where the part of object to be measured 200 such as the forearm part is inserted in the container 106, and the optical interface member 20 is injected from the reservoir 114 into each bag 106b by use of the pump 112 to such an extent that the gap between the container outer wall 106a and the part of object to be measured 200 is filled therewith. The pressure gauge 116 makes it possible to monitor whether an excessive pressure which may damage the part of object to be measured 200 is exerted thereon or not at the time of injecting the optical interface member 20, and monitor whether the internal pressure of the optical interface member 20 is kept uniform or not at the time of measurement.

Using the above-mentioned container 106 prevents the optical interface member 20 from leaking out of the container 106, thereby facilitating the replacement, storage, and the like of the container. Also, since the optical interface member 20 does not come into direct contact with the part of object to be measured 200, the container is free of uneasiness and is applicable to cases where the status changes drastically such as those during exercises.

Though the container has a cylindrical form in each of the above-mentioned modified examples, it can be changed to various forms such as conical and cup-like forms in view of the form of the part of object to be measured 200, easiness in measurement and calculations, and the like.

What is claimed is:

1. An optical CT apparatus for measuring optical characteristics of a part of an object having a predetermined optical characteristic, the apparatus comprising:

a container for storing a light-transparent medium having an optical characteristic substantially identical, in at least one of a scattering and an absorption coefficient, to an average value of the optical characteristic of the part of the object being measured;

light-projecting means for projecting light into said container;

light-detecting means for detecting to light protected by said light projecting means; and arithmetic means receiving a projection signal relating to the light projected by said light projecting means and a detection signal relating to the light detected by said light-detecting means, for determining a first characteristic amount relating to an optical characteristic of a scattered light that is transmitted through the medium and measured by use of said light projection means and said light detecting means in a state where the medium is stored within said container, for determining a second characteristic amount relating to an optical characteristic of a scattered light that is transmitted through the medium, and/or the part of the object being measured, and measured by use of said light projection means and said light detecting means in a state where the medium is at least partly replaced by the part of object to be measured, and for calculating a spatial distribution of a characteristic amount of the next of the object to be measured according to a comparison of the first characteristic amount with the second characteristic amount;

wherein said arithmetic means comprises:

first arithmetic means for assuming the inside of said container to be an assembly model divided into a plurality of volume elements and calculating a degree of influence of a change in a characteristic amount relating to an optical characteristic of each volume element upon a characteristic amount relating to an optical characteristic of the transmitted light detected by said light-detecting means in a case where said light-projecting means and said light-detecting means are used;

second arithmetic means for calculating an amount obtained when an optical amount concerning an optical characteristic of the light transmitted through the medium and measured by use of said light-projecting means and said light-detecting means in a state where the medium is accommodated within said container and an optical amount concerning an optical characteristic of the light transmitted through the medium and/or the part of object to be measured and measured by use of said light-projecting means and said light-detecting means in a state where the medium is partly replaced by the part of the object being measured are compared with each other; and third arithmetic means for calculating a spatial distribution of a characteristic amount relating to an optical characteristic of the part of object being measured by calculating a characteristic amount relating to an optical characteristic of each volume element from the degree of influence determined by said first arithmetic means and the amount determined by said second arithmetic means from the comparison of the characteristic amounts relating to optical characteristics.

2. An optical CT apparatus according to claim 1, wherein the characteristic amount relating to the optical characteristic of transmitted light is an optical intensity transmitted light.

3. An optical CT apparatus according to claim 1, wherein the characteristic amount relating to the optical characteristic of the part of the object being measured is an absorption coefficient of the part of the object being measured.

4. An optical CT apparatus according to claim 1, wherein the medium has a refractive index substantially identical to an average value of a refractive index of the part of the object being measured.

5. An optical CT apparatus according to claim 1, further comprising light-shielding mean; provided in an opening portion of said container, for blocking external light.

6. An optical CT apparatus according to claim 1, further comprising pressure reducing means for reducing a pressure within said container.

7. An image reconstructing method comprising:

a first measurement step of projecting light into a container storing therein a light-transparent medium having an optical characteristic substantially identical, in at least one of a scattering or absorption coefficient, to an average value of an optical characteristic of the part of the object being measured, by using light-projecting means, and detecting the light projected by said light-projecting means by using light-detecting means, so as to obtain a characteristic amount relating to an optical characteristic of a scattering light transmitted through the medium:

a second measurement step of projecting light into said container by using said light projecting means in a state where the medium stored within said container is partly replaced by a part of an object being measured, and detecting the light projected by said light projecting means by using said light-detecting means so as to obtain a characteristic amount relating to an optical characteristic of a scattering light transmitted through the medium and/or the part of object being measured; and an arithmetic step of calculating a spatial distribution of a characteristic amount relating to an optical characteristic of the part of the object being measured by calculating a characteristic amount relating to an optical characteristic of each volume element according to a comparison of the characteristic amount relating to the optical characteristic of the scattering light obtained by the first measurement step with the characteristic amount relating to the optical characteristic obtained by the second measurement step;

wherein the arithmetic step comprises:

a first arithmetic step of assuming the inside of said container to be an assembly model divided into a plurality of volume elements and calculating a degree of influence of a change in a characteristic amount relating to an optical characteristic of each volume element upon a characteristic amount relating to an optical characteristic of the transmitted light detected by said light-detecting means in a case where said light-projecting means and said light-detecting means are used;

a second arithmetic step of calculating an amount obtained when an optical amount relaxing to an optical characteristic of the light transmitted through the medium and measured by use of said light-projecting means and said light-detecting means in a state where the medium is accommodated within said container and an optical amount relating to an optical characteristic of the light transmitted through the medium and/or the part of object to be measured and measured by use of said light-projecting means and said light-detecting means in a state where the medium is at least partly replaced by the part of object being measured arc compared with each other; and a third arithmetic step of calculating a spatial distribution of a characteristic amount relating to an optical characteristic of the part of the object being measured by calculating a characteristic amount relating to an optical characteristic of each volume element from the degree of influence determined by the first arithmetic step and the amount obtained by the second arithmetic step from the comparison of the characteristic amounts relating to optical characteristics.

8. An image reconstructing method according to claim 7, wherein the characteristic amount relating to the optical characteristic of transmitted light is an optical intensity of transmitted light.

9. An image reconstructing method according to claim 7, wherein the characteristic amount concerning the optical characteristic of transmitted light is an absorption coefficient of the part of the object being measured.

10. An image reconstructing method according to claim 7, wherein the medium has an optics) characteristic substantially identical to an average value of an optical characteristic of the part of the object being measured.

11. An image reconstructing method according to claim 7, wherein the medium has an absorption coefficient substantially identical to an average value of on absorption coefficient of the part of the object being measured.

12. An image reconstructing method according to claim 7, wherein the medium has a scattering coefficient substantially identical to an average value of a scattering coefficient of the part of the object being measured.

13. An image reconstructing method according to claim 7, wherein the medium has a refractive index substantially identical to an average value of a refractive index of the part of the object being measured.

14. An image reconstructing method according to claim 7, wherein the medium has an optical rotation substantially identical to en average value of optical rotation of the of the object being measured.

15. An image reconstructing method according to claim 7, wherein the medium has a polarization degree substantially identical to an average value of polarization degree of the part of the object being measured.

* * * * *